United States Patent

Isogai

[11] Patent Number: 5,844,659
[45] Date of Patent: Dec. 1, 1998

[54] OPTHALMIC APPARATUS FOR MEASURING A REFRACTIVE POWER OF AN EYE TO BE EXAMINED

[75] Inventor: Naoki Isogai, Nishio, Japan

[73] Assignee: Nidek Co., LTD., Gamagori, Japan

[21] Appl. No.: 876,483

[22] Filed: Jun. 16, 1997

[30] Foreign Application Priority Data

Jun. 28, 1996 [JP] Japan .................................. 8-188567

[51] Int. Cl.⁶ .............................. A61B 3/14; A61B 3/10
[52] U.S. Cl. ............................. 351/208; 351/211
[58] Field of Search ................... 351/211, 208, 351/206, 205, 200, 221, 246, 212, 247

[56] References Cited

U.S. PATENT DOCUMENTS 5,406,076  4/1995  Mimura et al. .
5,463,430  10/1995  Isogai et al. .
5,625,428  4/1997  Isogai .................................. 351/208

FOREIGN PATENT DOCUMENTS 5-23302  2/1993  Japan .
7-163523  6/1995  Japan .
8-107881  4/1996  Japan .

*Primary Examiner*—Hung X. Dang
*Attorney, Agent, or Firm*—Oliff & Berridge, PLC

[57] ABSTRACT

An ophthalmic apparatus for measuring a refractive power of an eye to be examined, the ophthalmic apparatus providing an alignment detecting device for detecting an alignment condition of the apparatus corresponding to the eye to be examined by projecting a light so as to form a target onto the eye to be examined and detecting the target, a first judging device for judging whether the alignment condition of up-down/left-right directions is within a predetermined allowable condition based on the detected result of the alignment detecting device, a refractive power temporary measuring device for measuring a temporary refractive power value of the eye to be examined by generating a measurement start signal when it is judged by the first judging device that the alignment condition of up-down/left-right directions is within the predetermined allowable condition, variable means for varying an allowable condition of working distance based on a measured result of the refractive power temporary measuring device, and a second judging device for judging whether the eye to be examined is arranged within the allowable condition of working distance set by the variable device based on the detected result of the alignment detecting device.

14 Claims, 5 Drawing Sheets

OPTHALMIC APPARATUS FOR MEASURING A REFRACTIVE POWER OF AN EYE TO BE EXAMINED

BACKGROUND OF THE INVENTION

1. Field of the Invention

The present invention relates to an ophthalmic apparatus for measuring a refractive power of an eye to be examined for objectively measuring the refractive power of the eye.

2. Description of Related Art

An alignment adjustment mechanism of an ophthalmic apparatus for measuring a refractive power is well known in which an eye image to be examined which is displayed on a TV monitor for observation and a bright-point of corneal reflection by an alignment target projection are applied as a method. An operator observes the eye image and the bright-point of corneal reflection which are displayed on the TV monitor, and an alignment of the up-down/left-right directions is performed so that the bright-point of corneal reflection can be achieved to be a predetermined positional relation corresponding to a reticle on the TV monitor. Then, an alignment of working distance (the toward-away direction) is performed so as to focus on the bright-point of corneal reflection.

In the above-mentioned alignment adjustment mechanism, the alignment of the up-down/left-right directions can be performed comparative easily. However, a judging of working distance may be difficult, also it may be influenced depending on each individual different level of operator.

Therefore, there is proposed an apparatus which is provided a detecting mechanism for detecting an alignment condition, and when the alignment of the up-down/left-right directions and of working distance are completed and a predetermined condition of measurement start is achieved, the apparatus informs the operator that the predetermined condition of measurement start is achieved, or starts a measurement automatically.

However, if an allowable standard level of uniform working distance is provided like in conventional way and a condition of the allowable standard level is restricted, although a reliability of measured data may be improved, it may result in a disadvantage that a fulfilment of measurement start condition may be difficult, therefore a measurement cannot be started immediately. Contrarily, if the allowable condition of alignment is expanded (or loosen), even though the fulfilment of condition of measurement start can be achieved easily, it may result in another disadvantage that a measurement with sufficient accuracy can not be obtained when the refractive power is a high power.

SUMMARY OF THE INVENTION

The present invention has been made in view of the above circumstances and has an object to overcome the above problem and to provide an ophthalmic apparatus for measuring a refractive power of an eye to be examined, capable of achieving both a reliability of measured data and a simple measurement in equilibrium in accordance with the refractive power of the eye to be examined.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus for measuring a refractive power of an eye to be examined of this invention comprises alignment detecting means for detecting an alignment condition of the apparatus corresponding to the eye to be examined by projecting a light so as to form a target onto the eye to be examined and detecting the target, first judging means for judging whether an alignment condition of up-down/left-right directions is within a predetermined allowable condition, based on a detected result of the alignment detecting means, refractive power temporary measuring means for measuring a temporary refractive power value of the eye to be examined by generating a measurement start signal when it is judged by the first judging means that the alignment condition of up-down/ left-right directions is within the predetermined allowable condition, variable means for varying an allowable condition of working distance based on a measured result of the refractive power temporary measuring means, and second judging means for judging whether the eye to be examined is arranged within the allowable condition of working distance set by the variable means based on the detected result of the alignment detecting means.

In another aspect of the present invention, the ophthalmic apparatus comprises alignment means for detecting an alignment condition of the apparatus corresponding to an eye to be examined, refractive power temporary measuring means for measuring a temporary refractive power value after alignment of up-down/left-right directions is completed based on a detected result of the alignment means, variable means for varying an allowable condition of working distance based on a measured data by the refractive power temporary measuring means, detecting means for detecting a distance relation of the apparatus corresponding to the eye to be examined and detecting an alignment condition, and judging means for judging whether the eye to be examined is arranged within a range of allowable condition set by the variable means based on the detected result by the detecting means.

Also, in another aspect of the present invention, the ophthalmic apparatus comprises alignment detecting means for detecting an alignment condition of the apparatus corresponding to an eye to be examined, first refractive power measuring means for measuring the refractive power of the eye to be examined based on a detected result by the alignment detecting means, variable means for varying an allowable condition of working distance based on a measured result which is obtained by the first refractive power measuring means, working distance judging means for judging whether the eye to be examined is arranged within a range of allowable condition of working distance set by the variable means based on the detected result of the alignment detecting means, and second refractive power measuring means for measuring a refractive power of the eye to based on a judged result by the judging means.

As described above, according to the present invention, the apparatus enables to achieve a measurement with sufficient accuracy and simple measurement in equilibrium with high standard level.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention.

In the drawings.

DETAILED DESCRIPTION OF THE PREFERRED EMBODIMENTS

A detailed description of an ophthalmic apparatus for measuring a refractive power of an eye to be examined embodying the present invention will now be given referring to the accompanying drawings.

[General constitution]

Figure 1:
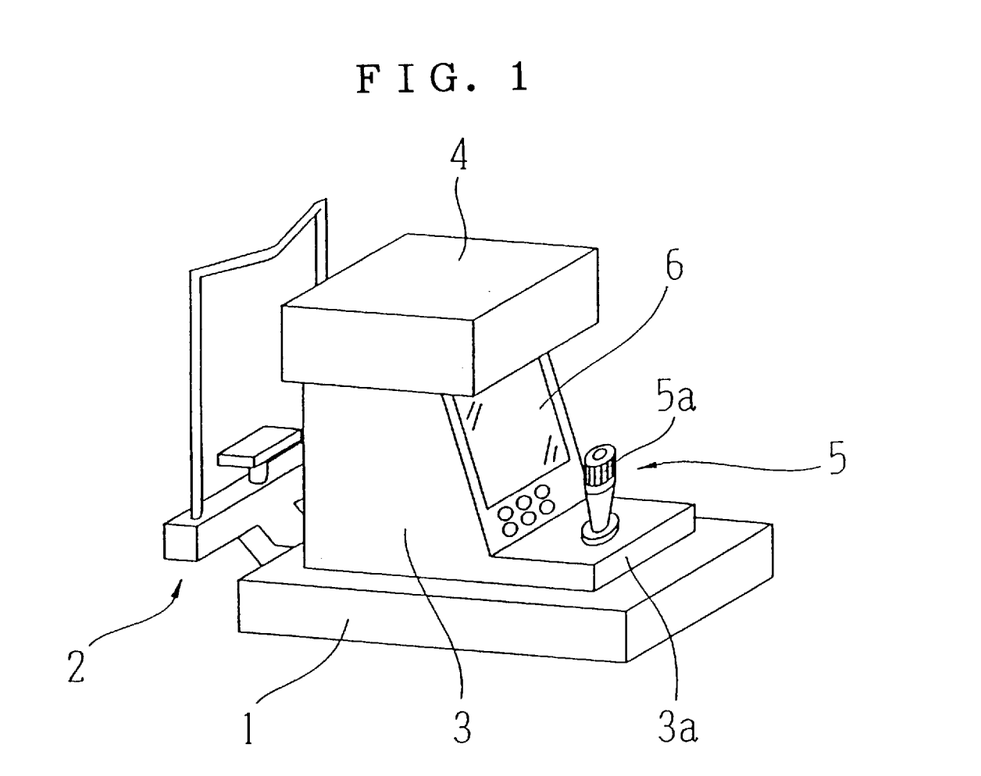
FIG. 1 is a view showing a outline diagram of outward shape of the preferred embodiment of the present invention.

FIG. 1 is a view showing a outline diagram of outward shape of the preferred embodiment. Reference numeral 1 denotes a base table, on which a chin support member 2 is set to fix an eye to be examined. Reference numeral 3 is a body unit and 4 is a measuring unit having an optical system which will be described hereinafter. Reference numeral 5 is a joystick for shifting the body unit 3 and the measuring unit 4. By handling the joystick 5, the body unit 3 is slid on a horizontal plane of the base table 1 in the toward-away and left-right directions, and the measuring unit 4 is shifted up and down opposite to the body unit 3. With respect to a shifting of the body unit opposite to the base table 1, a spherical part and bottom part which are formed under a shaft of the joystick 5, a sliding plate for sliding by the bottom part, a friction plate which is touched to the sliding plate and attached to the base table 1, and a spherical shaft receiver within a housing 3a which is connected with the body unit 3 are constituted so as to achieve an oscillation of a horizontal direction. Further, regard as an up-down shifting of the measuring unit 4 opposite to the body unit 3, due to a constitution of a rotating knob 5a on the peripheral top part of the joystick 5, a slit-plate which is rotated with the rotating knob 5a, and a light source and photodetector which put the slit-plate between them and is provided for the shaft, a rotating direction and rotation number of the rotating knob 5a are detected by a signal of the photodetector, thereby a motor for the up-down shifting of the measuring unit 4 is driven and controlled based on the detected result. The detail of the joystick is described in Japanese Laid-open No. 6-7292 by the present applicant, corresponding to the is disclosed in U.S. Pat. No. 5,406,076 granted to the applicant of the present patent application.

Reference numeral 6 denotes a TV monitor for displaying an eye image to be examined and information for informing the operator.

[Optical system]

Figure 2:
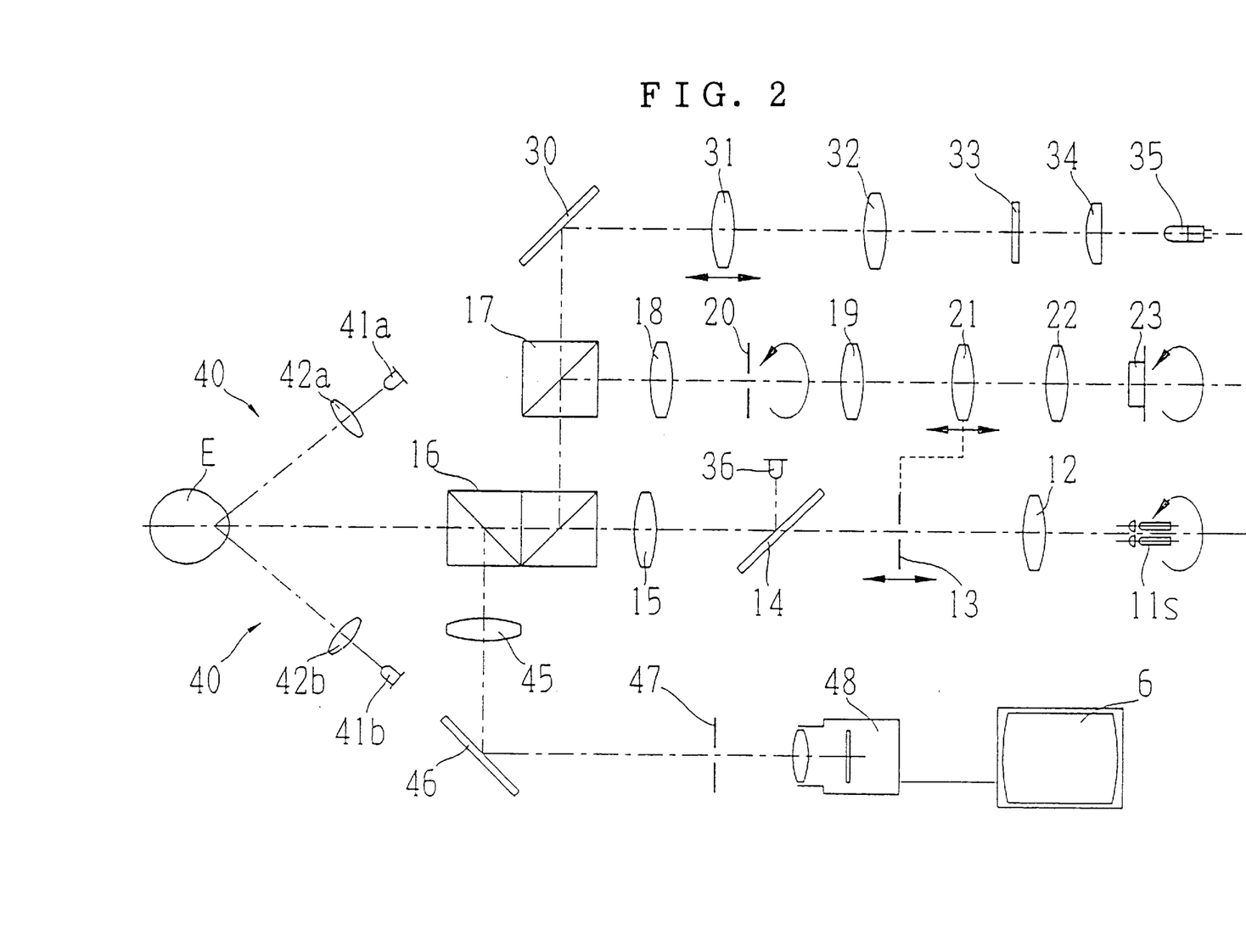
FIG. 2 is a diagram showing a outline arrangement of optical system of the preferred embodiment of the present invention viewed from the upper angle.

FIG. 2 is a diagram showing a outline arrangement of optical system of the preferred embodiment viewed from the upper angle. The detail of each optical system of the ophthalmic apparatus such as a measurement optical system, a fixation target optical system, an alignment target projection optical system and an observation optical system will be described respectively herein.

(Measurement optical system)

Reference numeral 11s denote two light sources having a wavelength in an infrared region, and they are disposed so as to enable to be rotated around the optical axis. Reference numeral 12 is a condenser lens, thereby the light sources 11s are positioned at a front focal point of the condenser lens 12. Reference numeral 13 is a target plate for measurement which has a target for measurement (spot aperture) and is movable to be disposed at a conjugate position relative to a fundus of an eye E to be examined. Reference numeral 14 is a beam splitter, which is coaxial with an optical axis of a first target projection optical system that will be described hereafter. Reference numeral 15 is a projection lens so as to project the target for measurement on the fundus of the eye E.

Reference numeral 16 and 17 are beam splitters. Reference numeral 18 and 19 are relay lenses, 20 is a belt-type corneal reflecting rejection mask which is disposed at a conjugate position relative to a cornea of the eye E, 21 is a movable lens which is moved with the target 13, 22 is an image-forming lens. Reference numeral 23 is a photodetector for measurement, and the photodetector 23 is rotated around the optical axis by synchronizing with the light sources 11s for measurement and the corneal reflecting rejection mask 20.

(Fixation target optical system)

Reference numeral 30 is a mirror, 31 is a first relay lens which is movable on the optical axis, and the eye to be examined is fogged by a movement of the first relay lens on the optical axis. Reference numeral 32 is a second relay lens, 33 is a fixation target which is disposed at a focal point of the second relay lens 32, 34 is a condenser lens, and 35 is a illumination lamp.

(Alignment target projection optical system)

An alignment target projection optical system is constituted by a first target projection optical system for projecting a target from a visual axial direction, and a second target projection optical system having an optical axis with a certain angle opposite to the first target projection optical system.

The first target projection optical system has a following constitution. Reference numeral 36 is a point light source for emitting an infrared light, the point light source 36 is disposed at the front focal point of the projection lens 15 passed through the beam splitter 14. A luminous flux emitted from the point light source 36 is changed to be a parallel luminous flux by the projection lens 15, thereby an image of point light-source is formed by corneal reflection of the eye E.

Figure 3:
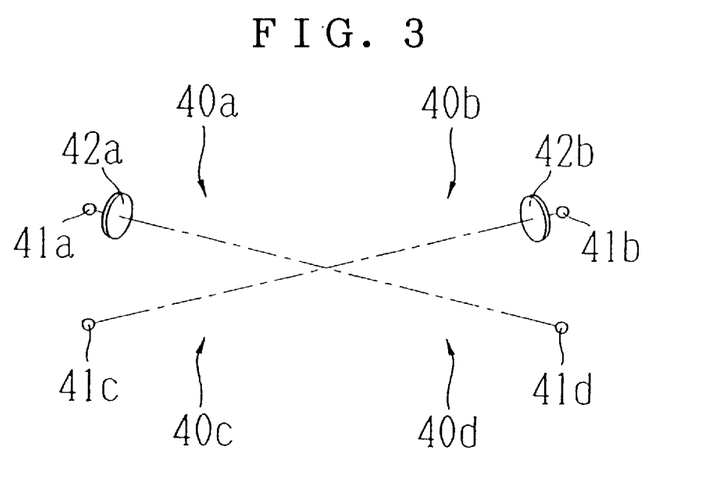
FIG. 3 is a view showing a second target projection optical system in FIG. 2 viewed from an examinee's side.

Reference numeral 40 is the second target projection optical system, wherein 4 pairs (40a–40d) of projection optical systems are disposed so as to cross measurement optical axis in the center, also each projection optical system is disposed with holding a predetermined angle opposite to the measurement optical axis. FIG. 3 is a view showing a second target projection optical system 40 viewed from an examinee's side. The projection optical system 40a and 40b comprise the point light sources 41a and 41b for emitting the infrared light and collimating lenses 42a and 42b respectively, so that an infinite target is projected from a top of slanting direction opposite to the eye E. The projection optical system 40c and 40d comprise the point light sources 41c and 41d for emitting the infrared light, so that a finite target is projected from a bottom of slanting direction opposite to the eye E. The image of corneal reflection is formed at a periphery to cornea of the eye to be examined by these projection optical systems 40a–40d. Therefore, the reflection light caused by the corneal reflection is not turned into the measurement optical system, also without taking measures to remove the reflection light at the cornea, the influence on the measurement optical system can be avoided.

(Observation optical system/Alignment target detecting optical system)

After the luminous flux from an anterior part of the eye to be examined is reflected at the beam splitter 16, the luminous flux is photographed by a CCD camera 48 passed through an objective lens 45, a mirror 46 and a telecentric diaphragm 47. An anterior part image of the eye E and the corneal reflection image of four light sources 41s and the light source 36 photographed by the CCD camera 48 are displayed on the TV monitor 6.

Also, the alignment condition is detected by a position of the corneal reflection image photographed by the CCD camera 48.

[Electric system]

Figure 4:
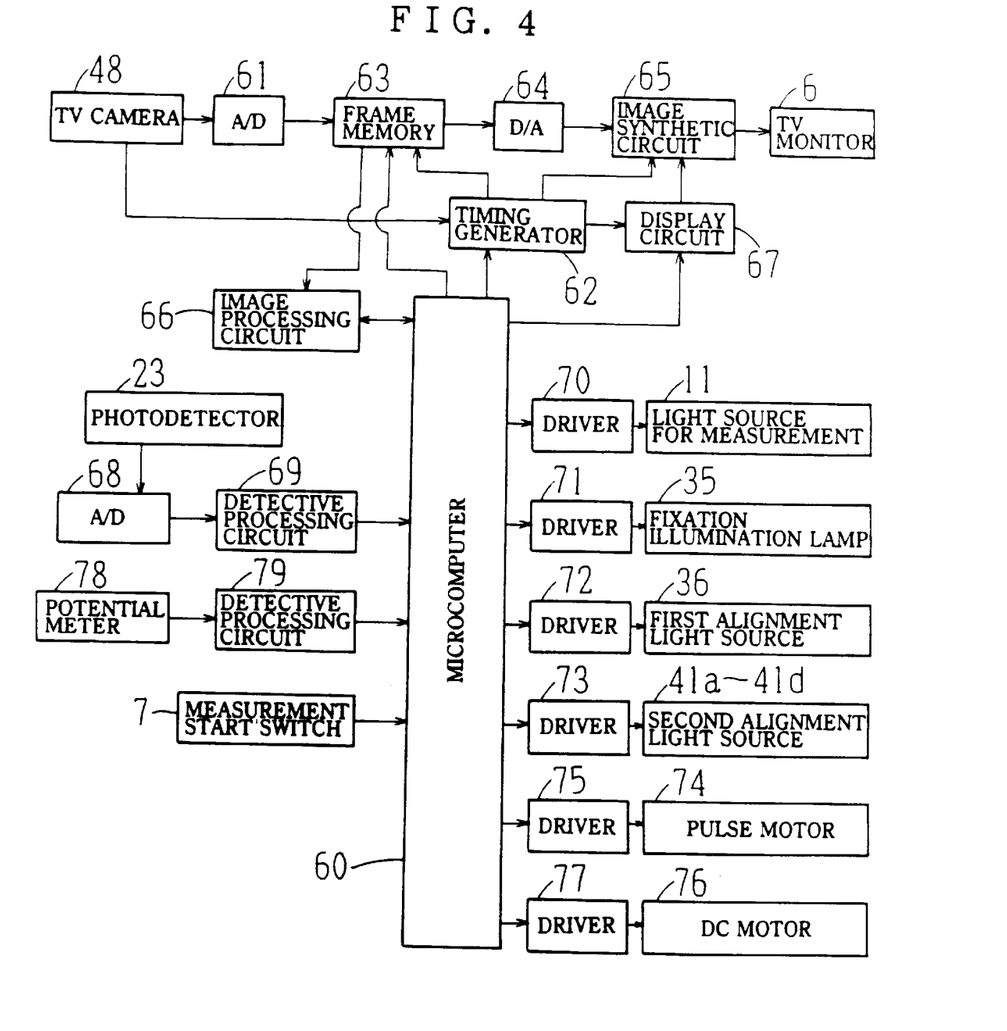
FIG. 4 is a detail view showing a block diagram of electric system of the preferred embodiment of the present invention.

FIG. 4 is a detail view showing a block diagram of electric system of the preferred embodiment.

A video signal from the CCD camera 48 is digitized by an A/D converter 61, thereby the video signal is taken into a frame memory 63 by synchronizing with a signal of a timing generator 62. An image taken into the frame memory 63 is displayed simultaneously on the TV monitor 6 passed through a D/A converter 64 and an image synthetic circuit 65.

Reference numeral 66 is a image processing circuit for processing the image which is taken into the frame memory 63 so as to detect the alignment target image, and a microcomputer 60 controls that a coordinate point of target image is obtained by a signal from the image processing circuit 66.

Reference numeral 67 is a display circuit for producing reticle marks, graphics, characters information or the like in order to display on the TV monitor 6, thereby a signal from the display circuit 67 is synthesized with a picture signal from the CCD camera 48 by the image synthetic circuit 65 so as to display on the TV monitor 6.

Reference numeral 68 is a A/D converter, after a signal from the photodetector 23 is digitized by the A/D converter 68, a predetermined measures is carried out by a detective processing circuit 69 so as to input the signal into the microcomputer 60.

Reference numeral 70 is a driver for driving the light sources 11s for measurement, 71 is a driver for driving the illumination lamp 35 for illuminating the fixation target, 72 is a driver for driving the point light source 36, and 73 is a driver for driving the light sources 41a–41d. Reference numeral 74 is a pulse motor for rotating the light sources 11s for measurement, the corneal reflecting rejection mask 20 and the photodetector 23, and 75 is a driver for driving the pulse motor 74. Reference numeral 76 is a DC motor for moving the target plate 13 for measurement and the movable lens 21, and 77 is a driver for driving the DC motor 76. Reference numeral 78 is a potential meter for detecting a moved position of the target plate 13 for measurement, and 79 is a detective processing circuit for taking a predetermined processing for a signal from the potential meter 78.

Next, the operation method for the above-mentioned apparatus will be described herein.

Figure 5:
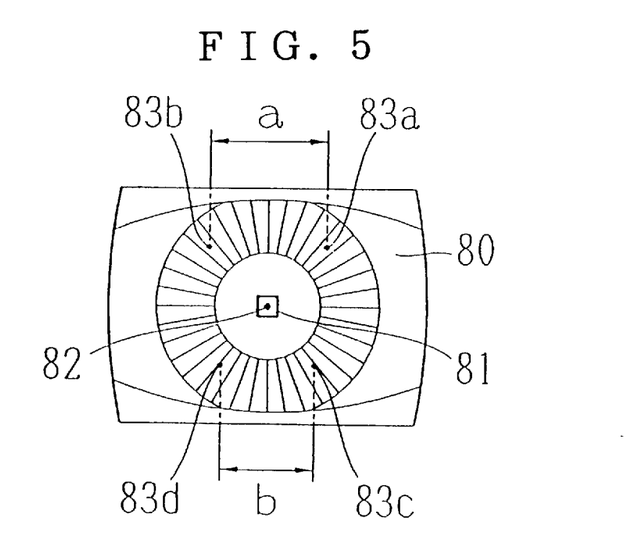
FIG. 5 is a view showing a display sample which is displayed on a TV monitor upon alignment.

The eye E is placed at a predetermined position by use of the chin support material 2, and each light source is turned on by the operator. The anterior part image which is illuminated by the illumination light source for anterior part not illustrated herein and the corneal reflection image of the light source 36 and the light sources 41a–41d by the alignment target projection optical system are caught by the CCD camera 48, so that they are displayed on the TV monitor 6. FIG. 5 shows a display sample upon this process. Reference numeral 80 is an anterior part, 81 is an aiming mark which is formed electrically by the display circuit 67 (the aiming mark may be also formed optically). Reference numeral 82 is a target image of the light source 36 in the first target projection optical system which is formed by corneal reflection, and reference numeral 83a–83d are target images by the corneal reflection of the point light sources 41a–41d in the second target projection optical system 40.

While observing the TV monitor 6, the operator focuses roughly such as target image 82, so that the measuring unit 4 is shifted by handling the joystick 5 and the rotating knob 5a so as to position the target image 82 in the center of the aiming mark 81. Then the alignment adjustment of the up-down/left-right directions for optical system (measuring unit 4) corresponding to the eye to be examined is performed.

By the microcomputer 60, the target image 82 positioned in the center is extracted from among five target images which are detected by the signal from the image processing circuit 66, and then the alignment condition of the up-down/left-right directions in the measuring unit 4 (measurement optical system) opposite to the eye to be examined is sensed so as to obtain a shifting distance of image target from the optical axis. Further, the microcomputer 60 judges whether the obtained shifting distance is within the predetermined allowable condition, and when it is judged that the shifting distance is within the predetermined allowable condition, a temporary measurement is started by generating a measurement start signal (regarding the alignment condition of working distance, in case that incident light quantity of target luminous flux toward the CCD camera 48 can be obtained more than a predetermined threshold level, also to the extent that target image can be obtained, the temporary measurement may be performed).

The microcomputer 60 controls that the light sources 11s for measurement are turned on by the measurement start signal. A measurement luminous flux emitted from the light sources 11s for measurement is passed through the condenser lens 12, the target plate 13, the beam splitter 14, the projection lens 15 and the beam splitter 16 so as to be condensed at an adjacent to a cornea of the eye E, then the luminous flux reaches at the fundus of the eye. In case of a normal eye without ametropia, the target image reflected at the fundus is reflected at the beam splitter 17 and passed through the relay lenses 18 and 19, thereby the target image is formed on the photodetector 23 by the image-forming lens 22. In case of an eye with ametropia, based on the received signal of reflection light at the fundus which is received by the photodetector 23, the microcomputer 60 drives the DC motor 76 for moving the movable lens 21 and the target plate 13 so as to be disposed at a conjugate position relative to the fundus of the eye E. The moved position is detected by the potential meter 78 so as to obtains a temporary refractive power value at a certain diameter (a refractive power of a plural up-down directions may be obtained by rotating the light sources 11s for measurement, the corneal reflecting rejection mask 20 and the photodetector 23).

Since the alignment adjustment of working distance direction is not performed precisely, the obtained refractive power value includes some errors. However, even though the alignment adjustment of working distance is not performed completely, it is less possible that the measured refractive power value deviates shapely from the actual refractive power value of the eye to be examined (for instance, if 10 mm of the working distance deviates to the extent that the target image can be obtained, even though −10D is obtained as the temporary refractive power value, the error may be about ±1D compared with the refractive power value which is measured under the proper alignment condition), therefore the allowable condition of working distance is set based on the temporary refractive power value which is obtained by the above-mentioned process.

Next, a setting process for the allowable condition of working distance will be described herein.

In case that a necessary accuracy of measured result is obtained at 0.25D step, if a diopter variation caused by a displacement of working distance from a proper position is within 0.12D, the variation of measured result may be not influenced. As a result of this, a relation between displacement x(mm) of working distance from an allowable proper position and refractive power is expressed by the following formula.

$$1000/f - 1000/(f+x) = 0.12$$

Besides, "f" in the above formula denotes a value when the refractive power value (diopter) is transposed to a focal distance (f=1000/D).

In accordance with the above-mentioned formula, the microcomputer 60 calculates "f" from the refractive power value obtained by the temporary measurement, thereby "f" is substituted for the above-mentioned formula so as to find the displacement "x", in other word, the allowable condition of working distance corresponding to the refractive power value, so that the allowable working distance is set for the actual measurement. Consequently, for the allowable condition of working distance necessary for a condition that refractive power is high, when the refractive power is low, even though the allowable condition is expanded, a measurement with sufficient accuracy can be achieved.

Figure 6:
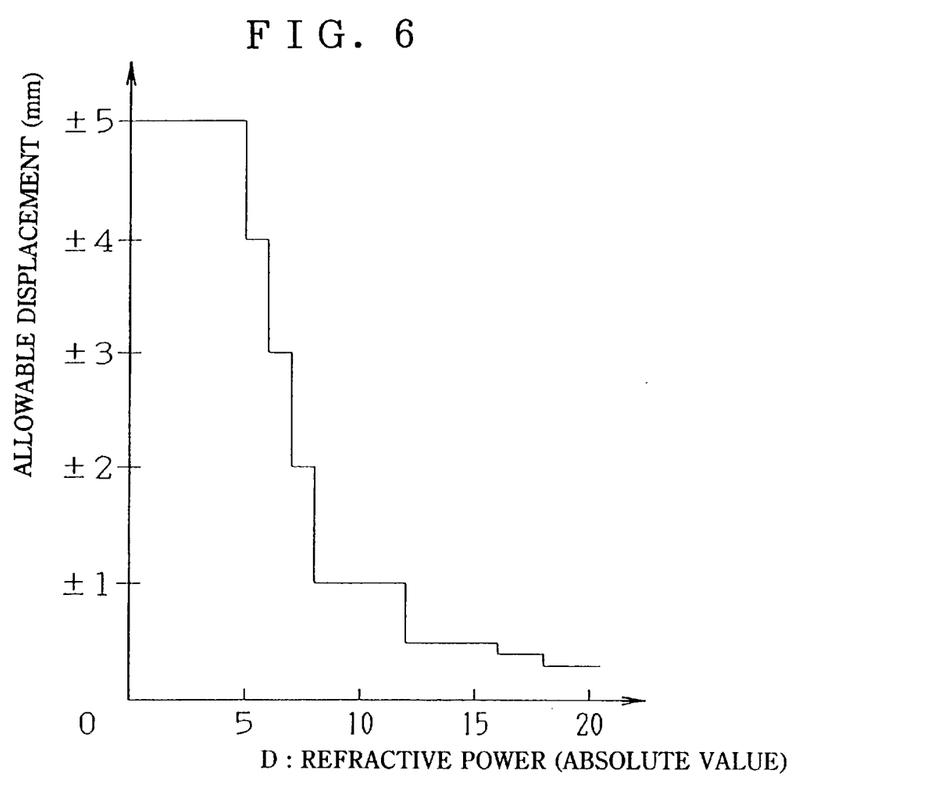
FIG. 6 is a view showing a table sample for a setting of working distance in accordance with a refractive power value.

Further, regarding the setting of allowable working distance, without depending on the above-mentioned formula, it is more convenient that the table for setting a working distance according to refractive power should be stored beforehand. As one sample shown in FIG. 6, the displacement corresponding to the refractive power calculated by the above-mentioned formula is set at a range level of plural steps. By narrowing the allowable working distance more than the above- mentioned value, the higher accuracy can be also improved.

As following this step, when the refractive power value is calculated by the temporary measurement, the microcomputer 60 varies the allowable condition of working distance based on the refractive power value.

After the alignment adjustments of the up-down/left-right directions are completed, the operator handles the joystick 5 in order to shift the optical system (the measuring unit 4) in the toward-away direction opposite to the eye to be examined, so that the alignment adjustment of working distance is performed. The apparatus provides means for judging-the alignment condition of working distance by detecting the target image in the second target projection optical system.

The judging of the alignment condition of working distance will be described herein. The microcomputer 60 calculates respectively a distance between the target image 83a and 83b which are processed by the image processing circuit 66 and obtained, and a distance between the target image 83c and 83d. Since the target images 83a and 83b are images of light sources which are disposed optically at an infinite distance, even though the apparatus deviates in the direction of working distance, the distance between the target images 83a and 83b is hardly different. On the other hand, since the target images 83c and 83d are images of light sources which are disposed optically at a finite distance, its distance is changed depending on the displacement of working distance of the apparatus. The detail of this relation is described in Japanese Laid Open No. 6-46999 corresponding to U.S. Pat. No. 5,463,430 by the present applicant as a reference.

By applying the characteristic of the above-mentioned relation, assuming the distance between the target images 83a and 83b is "a", also the distance between the target images 83c and 83d is "b", when a formula for finding a distance between the eye to be examined and the apparatus is set, b/a=S, (S is a value with a range relative to the allowable range of set working distance based on the temporary refractive power value), the alignment condition of working distance can be detected as follows.

(A) b/a>S indicates that the eye to be examined is shifted forward.

(b) b/a=S indicates that alignment of working distance is completed.

(c) b/a<S indicates that the eye to be examined is shifted backward.

Figure 7:
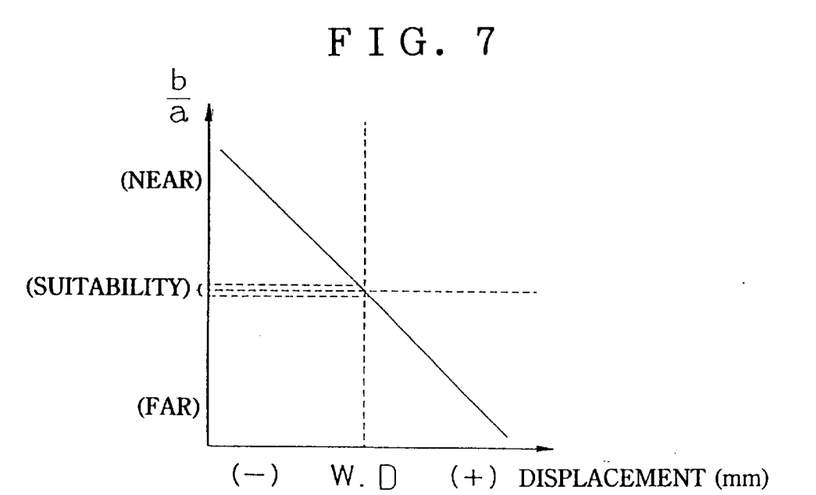
FIG. 7 is a view explaining a detection of displacement of working distance.

Also, it is possible to know the displacement of working distance by beforehand calculating information of relation to a value of "b/a" such as shown in FIG. 7.

Incidentally, regarding the target projection optical system for projecting a finite target of the second target projection optical system and the target projection optical system for projecting an infinite target, at least a pair of optical system may be disposed symmetrically around the measurement optical axis. In this case, the judging of the alignment condition is performed by comparison between a distance of finite target image and a distance of infinite target image corresponding to a vertex of cornea (the vertex of corneal can be obtained from a position of target image by the first target projection optical system).

The microcomputer 60 controls that a command is displayed on the TV monitor 6 so as to inform the operator of a moving direction of the measuring unit 4 based on the judging of the alignment condition of working distance. As a displaying method, such an arrow mark may be available for indicating a direction directly, or another indication point mark which is conditioned beforehand may be available as well. The indication display for indicating the moving direction is produced by the display circuit 67, so that it is displayed on the TV monitor 6 passed through the image synthetic circuit 65. The operator follows the indication display for moving direction and shifts the measuring unit 4 forward and backward by handling the joystick 5 so as to carry out the alignment adjustment of working distance (without displaying the indication for moving direction, the alignment adjustment may be performed so that the target image 82 can be brought into focus). At this time, since the allowable condition of alignment for working distance is set at a condition according to the refractive power of the eye to be examined, when the refractive power is a low power, a wide range of allowable condition is set, thereby the alignment adjustment of working distance can be completed easily. Also, when it is a high power, the alignment for achieving a measurement with sufficient accuracy can be completed.

When the microcomputer 60 judges that the alignment for working distance is completed (within the allowable condition set by the above-mentioned temporary refractive power value) and confirms that the alignment condition of the up-down/left-right directions is within the predetermined allowable condition, the measurement start signal for the actual measurement is generated automatically so as to execute the actual measurement (the completion of alignment is displayed on the TV monitor 6, or is informed the operator by sound, so that the operator may press the measurement start switch 7 for starting the measurement). The actual measurement is to be performed as follows. As the same process of the temporary measurement, the target image is projected on the fundus of the eye to be examined by turning on the light sources 11s for measurement, thereby the reflected target image at the fundus is detected by the photodetector 23. Based on the signal of the photodetector 23, the movable lens 21 and the target plate 31 are moved to be disposed at the conjugate position relative to the fundus. Next, after the first relay lens 31 is moved so as to dispose the fixation target 33 and the fundus of the eye E at the conjugate position relative to the eye to be examined. The first lens 31 is further moved so as to be covered with fog only for a portion of appropriated diopter. Under the condition that the eye E is fogged, the light sources 11s for measurement, the corneal reflecting rejection mask 20 and the photodetector 23 are rotated 180 degree around the optical axis. During the rotation, the target plate 13 and the movable lens 21 are moved by the signal from the photodetector 23, so that the movement distance is detected by the potential meter 78 so as to find the refractive power value of each diameter direction. The microcomputer 60 calculates the refractive power of the eye to be examined by taking a predetermined processing for this refractive power value. The measured result is displayed on the TV monitor 6.

When the continuous measurement of the same eye to be examined is performed, the allowable condition of alignment for working distance is set based on the refractive power value which is obtained by the actual measurement (when a plural measurement is performed, a latest result of the refractive power value should be utilized). Also, when the eye to be examined is exchanged, the setting of allowable condition of alignment for working distance is needed to be clear by a change-over signal.

As described in the above, a relative movement like in the up-down, left-right and working-distance directions of the measuring unit 4 opposite to the eye to be examined is to be performed by manual operation that the operator handles the joystick 5. But as another method, a moving mechanism may be provided for electrically moving the measuring unit 4 in each directions or a particular direction by use in a motor. Accordingly, the alignment adjustment can be performed automatically based on the detected result of the alignment condition.

Furthermore, although an installed-type apparatus is explained as a technical art in the preferred embodiment, a hand-held type apparatus can be also utilized in the same method.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for measuring a refractive power of an eye to be examined, the ophthalmic apparatus comprising:

alignment detecting means for detecting an alignment condition of the apparatus corresponding to the eye to be examined by projecting a light so as to form a target onto the eye to be examined and detecting the target;

first judging means for judging whether an alignment condition of up-down/left-right directions is within a predetermined allowable condition based on a detected result of said alignment detecting means;

refractive power temporary measuring means for measuring a temporary refractive power value of the eye to be examined by generating a measurement start signal when it is judged by said first judging means that the alignment condition of up-down/ left-right directions is within the predetermined allowable condition;

variable means for varying the allowable condition of working distance based on a measured result of said refractive power temporary measuring means; and second judging means for judging whether the eye to be examined is arranged within the allowable condition of working distance set by said variable means based on the detected result of said alignment detecting means.

2. The ophthalmic apparatus according to claim 1, further comprising allowable condition control means for controlling the allowable condition of working distance which is varied by said variable means such as the allowable condition is to be expanded when the refractive power is a low power compared with a high power.

3. The ophthalmic apparatus according to claim 1, further comprising memory means for storing a table for setting the working distance necessary for the temporary refractive power value which is obtained by said refractive power temporary measuring means, whereby the allowable condition of working distance being varied by said variable means based on said table which is stored by said memory means.

4. The ophthalmic apparatus according to claim 1, further comprising calculation means for calculating the working distance necessary for the temporary refractive power value which is obtained by said refractive power temporary measuring means, whereby the allowable condition of working distance being varied by said variable means based on the calculated result by said calculation means.

5. The ophthalmic apparatus according to claim 1, further comprising actual measurement start signal generating means for generating a measurement start signal for the actual measurement when it is judged by said first and second judging means that the alignment condition fulfills the predetermined allowable condition.

6. The ophthalmic apparatus according to claim 1, wherein said alignment detecting means includes, first target projection optical system for projecting an target for alignment onto a cornea of the eye to be examined from a visual axial direction of the eye to be examined;

first target image detecting means for detecting said first target image formed by said first target projection optical system;

second target projection optical system for projecting an target, which has different optical distance up to the eye to be examined, onto the eye;

second target image detecting means for detecting second target image formed by said second target projection optical system, whereby the alignment condition of the up-down/left-right directions being judged by said first judging means based on the detected result by said first target image detecting means, and the alignment condition of a toward-away direction being judged by said second judging means based on the detected result by said second target image detecting means.

7. The ophthalmic apparatus according to claim 6, wherein said first target image detecting means and said second target image detecting means are shared respectively.

8. An ophthalmic apparatus for measuring a refractive power of an eye to be examined, the ophthalmic apparatus comprising:

alignment means for detecting an alignment condition of the apparatus corresponding to an eye to be examined;

refractive power temporary measuring means for measuring a temporary refractive power value after alignment of up-down/left-right directions is completed based on a detected result of said alignment means;

variable means for varying an allowable condition of working distance based on a measured data by said refractive power temporary measuring means;

detecting means for detecting a distance relation of the apparatus corresponding to the eye to be examined and detecting an alignment condition; and judging means for judging whether the eye to be examined is arranged within a range of allowable condition set by said variable means based on the detected result by said detecting means.

9. The ophthalmic apparatus according to claim 8, further comprising allowable condition control means for controlling the allowable condition of working distance which is varied by said variable means such as the allowable condition is to be expanded when the refractive power is a low power compared with a high power.

10. The ophthalmic apparatus according to claim 8, further comprising memory means for storing a table for setting the working distance necessary for the temporary refractive power value which is obtained by said refractive power temporary measuring means, whereby the allowable condition of working distance being varied by said variable means based on said table which is stored by said memory means.

11. The ophthalmic apparatus according to claim 8, further comprising calculation means for calculating the working distance necessary for the temporary refractive power value which is obtained by said refractive power temporary measuring means, whereby the allowable condition of working distance being varied by said variable means based on the calculated result by said calculation means.

12. The ophthalmic apparatus according to claim 8, further comprising actual measurement start signal generating means for generating a measurement start signal for the actual measurement when it is judged by said judging means that the alignment condition fulfills the predetermined allowable condition.

13. An ophthalmic apparatus for measuring a refractive power of an eye to be examined, the ophthalmic apparatus comprising:

alignment detecting means for detecting an alignment condition of the apparatus corresponding to an eye to be examined;

first refractive power measuring means for measuring the refractive power of the eye to be examined based on a detected result by said alignment detecting means;

variable means for varying an allowable condition of working distance based on a measured result which is obtained by said first refractive power measuring means;

working distance judging means for judging whether the eye to be examined is arranged within a range of allowable condition of working distance set by said variable means based on the detected result of said alignment detecting means; and second refractive power measuring means for measuring the refractive power of the eye to be examined based on the judged result by said judging means.

14. The ophthalmic apparatus according to claim 13, wherein said alignment detecting means including up-down/left-right directions alignment detecting means for detecting the alignment condition of the up-down/left-right directions in the apparatus corresponding to the eye to be examined; and the apparatus further comprising:

up-down/left-right directions judging means for judging whether the alignment condition of the up-down/left-right directions is within the predetermined allowable condition based on the result by said up-down/left-right direction alignment detecting means; and measurement start signal generating means for generating a measurement start signal based on the judged result by said up-down/left-right directions judging means and said working distance judging means.

* * * * *